United States Patent
Colosi

(10) Patent No.: US 7,851,195 B2
(45) Date of Patent: *Dec. 14, 2010

(54) HIGH-EFFICIENCY WILD-TYPE-FREE AAV HELPER FUNCTIONS

(75) Inventor: Peter Colosi, Alameda, CA (US)

(73) Assignee: Genzyme Corporation, Framingham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/214,588

(22) Filed: Jun. 20, 2008

(65) Prior Publication Data

US 2009/0017542 A1    Jan. 15, 2009

Related U.S. Application Data

(63) Continuation of application No. 11/283,357, filed on Nov. 18, 2005, now abandoned, which is a continuation of application No. 10/074,302, filed on Feb. 11, 2002, now Pat. No. 7,037,713, which is a continuation of application No. 09/450,083, filed on Nov. 29, 1999, now Pat. No. 6,376,237, which is a continuation of application No. 09/143,270, filed on Aug. 28, 1998, now Pat. No. 6,001,650, which is a continuation-in-part of application No. 09/107,708, filed on Jun. 30, 1998, now Pat. No. 6,027,931, which is a continuation-in-part of application No. 08/688,648, filed on Jul. 29, 1996, now abandoned, which is a continuation-in-part of application No. 08/510,790, filed on Aug. 3, 1995, now Pat. No. 5,622,856.

(51) Int. Cl.
 *C12N 7/02* (2006.01)
(52) U.S. Cl. .................. 435/235.1; 435/325; 435/320.1
(58) Field of Classification Search ........................ None
See application file for complete search history.

(56) References Cited

U.S. PATENT DOCUMENTS

| | | | |
|---|---|---|---|
| 4,797,368 A | 1/1989 | Carter et al. | |
| 5,139,941 A | 8/1992 | Muzyczka et al. | |
| 5,173,414 A | 12/1992 | Lebkowski et al. | |
| 5,436,146 A | 7/1995 | Shenk et al. | |
| 5,589,377 A | 12/1996 | Lebkowski et al. | |
| 5,622,856 A | 4/1997 | Natsoulis | |
| 5,658,776 A | 8/1997 | Flotte et al. | |
| 5,693,531 A | 12/1997 | Chiiorini et al. | |
| 5,753,500 A | 5/1998 | Shenk et al. | |
| 6,001,650 A * | 12/1999 | Colosi ........................ 435/369 |
| 6,027,931 A | 2/2000 | Natsoulis et al. | |
| 6,365,403 B1 * | 4/2002 | Natsoulis et al. ............ 435/325 |
| 6,376,237 B1 * | 4/2002 | Colosi ..................... 435/320.1 |
| 7,037,713 B2 * | 5/2006 | Colosi ..................... 435/320.1 |

FOREIGN PATENT DOCUMENTS

| WO | WO 95/06743 A2 | 3/1995 |
|---|---|---|
| WO | WO 95/13365 A1 | 5/1995 |
| WO | WO 95/13392 A1 | 5/1995 |

OTHER PUBLICATIONS

Jayaram, "Two-Micrometer Circle Site-Specific Recombination: The Minimal Substrate and the Possible Role of Flanking Sequences," *PNAS USA* 82:5875-5879 (1985).
Karreman, et al., "On the Use of Double FLP Recognition Targets (FRTS) in the LTR of Retroviruses for the Construction of High Producer Cell Lines," *Nucl Acids Res* 24(9):1616-1624 (1996).
Li, et al., "Role for Highly Regulated Rep Gene Expression in Adeno-Associated Virus Vector Production," *J Virol* 71(7):5236-5243 (1997).
McCarty, et al., "Sequences Required for Coordinate Induction of Adeno-Associated Virus p19 and p40 Promoters by Rep Protein," *J Virol* 65(6):2936-2945 (1991).
O'Gorman, et al., "Recombinase-Mediated Gene Activation and Site Specific Integration in Mammalian Cells," *Science* 251:1351-1355 (1991).
Ogasawara, et al., "The Use of Heterologous Promoters for Adeno-Associated Virus (AAV) Protein Expression in AAV Vector Production," *Microbial Immunol* 42(3):177-185 (1998).
Samulski, et al., "Helper-Free Stocks of Recombinant Adeno-Associated Viruses: Mormal Integration Does Not Require Viral Gene Expression," *J Virol* 63(9):3822-3828 (1989).
Schlake, et al., "Use of Mutated FLP Recognition Target (FRT) Site for the Exchange of Expression Cassettes at Defined Chromosomal Loci," *Biochemistry* 33(43):12746-12751 (1994).
Vincent, et al., "Analysis of Recombinant Adeno-Associated Virus Packaging and Requirements for Rep and Cap Gene Products," *J Virology* 71(3):1897-1905 (1997).

* cited by examiner

*Primary Examiner*—James S Ketter
(74) *Attorney, Agent, or Firm*—Robins & Pasternak LLP

(57) ABSTRACT

The present invention provides methods and compositions for producing high titer, wild-type-free preparations of recombinant AAV ("rAAV") virions. The compositions of the present invention include novel nucleic acids encoding AAV helper functions and AAV helper function vectors. The present invention also includes host cells transfected by the claimed nucleic acids, methods of using the claimed vectors, and rAAV virions produced by such methods.

9 Claims, 6 Drawing Sheets

US 7,851,195 B2

HIGH-EFFICIENCY WILD-TYPE-FREE AAV HELPER FUNCTIONS

1. CROSS-REFERENCE TO RELATED APPLICATIONS

This application is a continuation of U.S. patent application Ser. No. 11/283,357, filed Nov. 18, 2005, which is a continuation of U.S. patent application Ser. No. 10/074,302, filed Feb. 11, 2002, which is a continuation of U.S. patent application Ser. No. 09/450,083, filed Nov. 29, 1999, now U.S. Pat. No. 6,376,237, which is a continuation of U.S. patent application Ser. No. 09/143,270, filed Aug. 28, 1998, now U.S. Pat. No. 6,001,650, which is a continuation-in-part of U.S. patent application Ser. No. 09/107,708, filed Jun. 30, 1998, now U.S. Pat. No. 6,027,931, which is a continuation-in-part of U.S. patent application Ser. No. 08/688,648, filed Jul. 29, 1996, now abandoned, which is a continuation-in-part of U.S. patent application Ser. No. 08/510,790, filed Aug. 3, 1995, now U.S. Pat. No. 5,622,856, from which applications priority is claimed pursuant to 35 U.S.C. §120, which applications are hereby incorporated by reference in their entireties.

2. FIELD OF THE INVENTION

The present invention relates to adeno-associated virus (AAV) helper function systems for use in recombinant AAV (rAAV) virion production. More specifically, the present invention relates to AAV helper function constructs that provide for high-efficiency rAAV production but do not generate wild-type AAV.

3. TECHNICAL BACKGROUND

Gene Therapy

Scientists are continually discovering genes that are associated with human diseases such as diabetes, hemophilia and cancer. Research efforts have also uncovered genes, such as erythropoietin (which increases red blood cell production), that are not associated with genetic disorders but code for proteins that can be used to treat numerous diseases. However, despite significant progress in the effort to identify and isolate genes, a major obstacle facing the biopharmaceutical industry is how to safely and persistently deliver effective quantities of these genes' products to patients.

Currently, the protein products of these genes are synthesized in cultured bacterial, yeast, insect, mammalian, or other cells and delivered to patients by intravenous injection. Intravenous injection of recombinant proteins has been successful but suffers from several drawbacks. First, patients frequently require multiple injections in a single day in order to maintain the necessary levels of the protein in the blood stream. Even then, the concentration of protein is not maintained at physiological levels—the level of the protein is usually abnormally high immediately following injection and far below optimal levels prior to injection. Second, intravenous delivery often cannot deliver the protein to the target cells, tissues or organs in the body. And, if the protein reaches its target, it is often diluted to non-therapeutic levels. Third, the method is inconvenient and severely restricts the patient's lifestyle. The adverse impact on lifestyle is especially significant when the patient is a child.

These shortcomings have led to the development of gene therapy methods for delivering sustained levels of specific proteins into patients. These methods allow clinicians to introduce DNA coding for a gene of interest directly into a patient (in vivo gene therapy) or into cells isolated from a patient or a donor (ex vivo gene therapy). The introduced DNA then directs the patient's own cells or grafted cells to produce the desired protein product. Gene delivery, therefore, obviates the need for daily injections. Gene therapy may also allow clinicians to select specific organs or cellular targets (e.g., muscle, liver, blood cells, brain cells, etc.) for therapy.

DNA may be introduced into a patient's cells in several ways. There are transfection methods, including chemical methods such as calcium phosphate precipitation and liposome-mediated transfection, and physical methods such as electroporation. In general, transfection methods are not suitable for in vivo gene delivery. There are also methods that use recombinant viruses. Current viral-mediated gene delivery methods include retrovirus, adenovirus, herpes virus, pox virus, and adeno-associated virus (AAV) vectors. Of the more than 100 gene therapy trials conducted, more than 95% used viral-mediated gene delivery. C. P. Hodgson, *Bio/Technology* 13, 222-225 (1995).

Adeno-Associated Virus-Mediated Gene Therapy

One viral system that has been used for gene delivery is adeno-associated virus (AAV). AAV is a parvovirus which belongs to the genus *Dependovirus*. AAV has several attractive features not found in other viruses. First, AAV can infect a wide range of host cells, including non-dividing cells. Second, AAV can infect cells from different species. Third, AAV has not been associated with any human or animal disease and does not appear to alter the biological properties of the host cell upon integration. Indeed, it is estimated that 80-85% of the human population has been exposed to the virus. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs). The ITRs are approximately 145 base pairs (bp) in length. The ITRs have multiple functions, including as origins of DNA replication and as packaging signals for the viral genome.

The internal non-repeated portion of the genome includes two large open reading frames, known as the AAV replication (rep) and capsid (cap) genes. The rep and cap genes code for viral proteins that allow the virus to replicate and package the viral genome into a virion. In particular, a family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus; that is, it requires co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. While AAV can infect cells from different species, the helper virus must be of the same species as the host cell. Thus, for example, human AAV will replicate in canine cells co-infected with a canine adenovirus.

AAV has been engineered to deliver genes of interest by deleting the internal non-repeating portion of the AAV genome (i.e., the rep and cap genes) and inserting a heterologous gene between the ITRs. The heterologous gene is typically functionally linked to a heterologous promoter (constitutive, cell-specific, or inducible) capable of driving gene expression in the patient's target cells under appropriate conditions. Termination signals, such as polyadenylation sites, can also be included.

To produce infectious rAAV containing the heterologous gene, a suitable producer cell line is transfected with an AAV vector containing a heterologous gene. The producer cell is concurrently transfected with a second plasmid harboring the AAV rep and cap genes under the control of their respective endogenous promoters or heterologous promoters. Finally, the producer cell is infected with a helper virus, such as adenovirus. Alternatively, the producer cell may be transfected with one or more vectors containing adenovirus accessory function genes.

Once these factors come together, the heterologous gene is replicated and packaged as though it were a wild-type AAV genome, forming a recombinant virion. When a patient's cells are infected with the resulting rAAV virions, the heterologous gene enters and is expressed in the patient's cells. Because the patient's cells lack the rep and cap genes and the adenovirus accessory function genes, the rAAV are replication defective; that is, they cannot further replicate and package their genomes. Similarly, without a source of rep and cap genes, wild-type AAV cannot be formed in the patient's cells.

Current methods of producing rAAV, however, present a number of significant problems. First, most of the current methods of producing rAAV yield viral titers that are too low to be therapeutically useful. Second, when an AAV vector carrying ITRs is introduced into a producer cell containing rep and cap genes, replication-competent pseudo-wild-type AAV may be produced by homologous and non-homologous recombination. Such pseudo-wild-type viruses carry the rep and cap genes sandwiched between the AAV ITRs. And, although wild-type AAV is not associated with any human or animal disease, clinicians would ideally prefer not to introduce any replication-competent viruses into already sick patients. Thus, it would be desirable to eliminate the production of pseudo-wild-type virus.

Many attempts have been made to deal with the problem of pseudo-wild-type formation, all of which have failed. Most recently, Shenk et al. (U.S. Pat. No. 5,753,500) claimed to have achieved wild-type-free stocks of rAAV. The helper vector used, pAAV/Ad, was constructed with AAV rep and cap genes located between adenovirus inverted terminal repeats, and all of the AAV helper vector's sequences homologous to AAV vector sequences were removed. Several laboratories have reported, however, that the pAAV/Ad helper vector generates between 0.01 and 10% wild-type AAV. This level of contaminating AAV is unacceptable for human clinical trials.

From the foregoing, it will be appreciated that it would be a significant advancement in the art to provide AAV helper functions for rAAV production that do not result in the formation of pseudo-wild-type AAV. It would be a further advancement in the art to provide such helper functions that allow high efficiency production of rAAV.

Such AAV helper functions and methods of their use are disclosed herein.

4. BRIEF SUMMARY OF THE INVENTION

The present invention relates to AAV helper functions for rAAV production. Provided herein are novel nucleic acid molecules that encode such AAV helper functions. In certain embodiments, the nucleic acid molecules of the present invention comprise an AAV rep coding region, an AAV cap coding region, and a modified AAV p5 promoter that lacks an intact TATA box. In certain preferred embodiments, the modified p5 promoter is situated 3' relative to the rep coding region. The nucleic acids of the present invention may be used to generate high titer stocks of rAAV but do not produce any detectable wild-type AAV.

The present invention also provides AAV helper function vectors that express Rep and Cap gene products. Such vectors may be constructed by linking the nucleic acid molecules of the present invention with suitable control sequences that direct the replication and expression of the resulting AAV helper function vectors. An AAV helper function vector of the present invention may be a plasmid, bacteriophage, transposon, cosmid, chromosome, artificial chromosome, virus, or other suitable genetic element, and may include selectable genetic markers such as antibiotic resistance genes. Such vectors may also include one or more accessory function genes, such as the E1A, E1B, E2A, VA RNA, and E4 regions of adenovirus.

Also provided herein are host cells for producing rAAV virions. In certain embodiments, a host cell of the present invention comprises a nucleic acid encoding AAV helper functions. Upon introduction of an AAV vector and expression of accessory functions in the host cell, rAAV virions are produced. In certain preferred embodiments, a host cell of the present invention also includes one or more accessory functions.

The present invention further provides methods of using accessory function vectors to produce rAAV and the rAAV virions produced by such methods. In certain embodiments, a method of the present invention includes the steps of (1) introducing an AAV vector into a suitable host cell; (2) introducing an AAV helper function vector of the present invention into the host cell; (3) expressing accessory functions in the host cell; and (4) culturing the host cell to produce rAAV virions. The AAV vector and AAV helper function vector can be transfected into the host cell, either sequentially or simultaneously, using well-known techniques. Accessory functions may be expressed in any of several ways, including infecting the host cell with a suitable helper virus (such as adenovirus, herpesvirus, or vaccinia virus), or by transfecting one or more accessory function vectors into the host cell. It is also well known in the art that certain cell lines, e.g., 293 cells, inherently express one or more accessory functions.

The rAAV virions produced using the present invention may be used to introduce genetic material into animals, including humans, or isolated animal cells for a variety of research and therapeutic uses. For example, rAAV virions produced using the methods of the present invention may be used to express a protein in animals to gather preclinical data or to screen for potential drug candidates. Alternatively, the rAAV virions may be used to transfer genetic material into a human to cure a genetic defect or to effect a desired treatment.

5. BRIEF SUMMARY OF THE DRAWINGS

Figure 5:
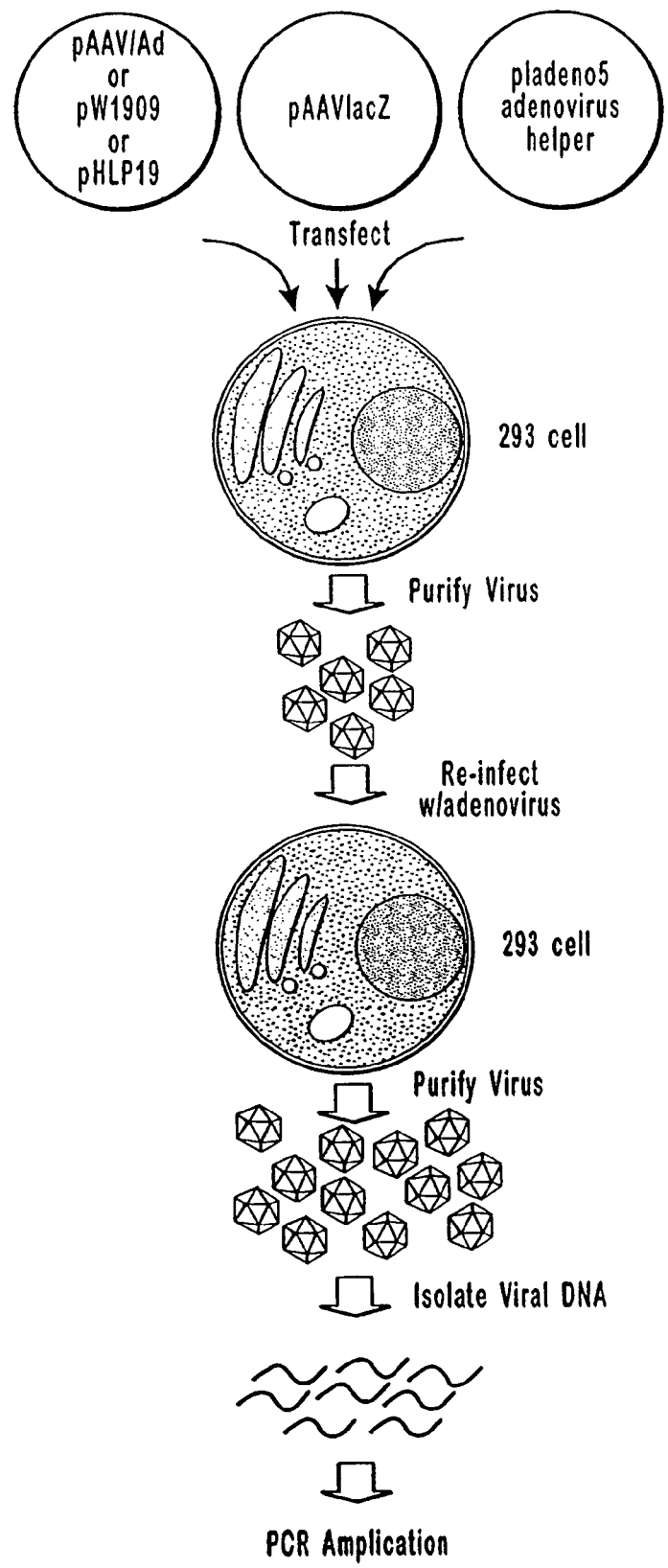

FIG. 5 schematically presents the method used to assay the production of pseudo-wild-type AAV.

Figure 6:
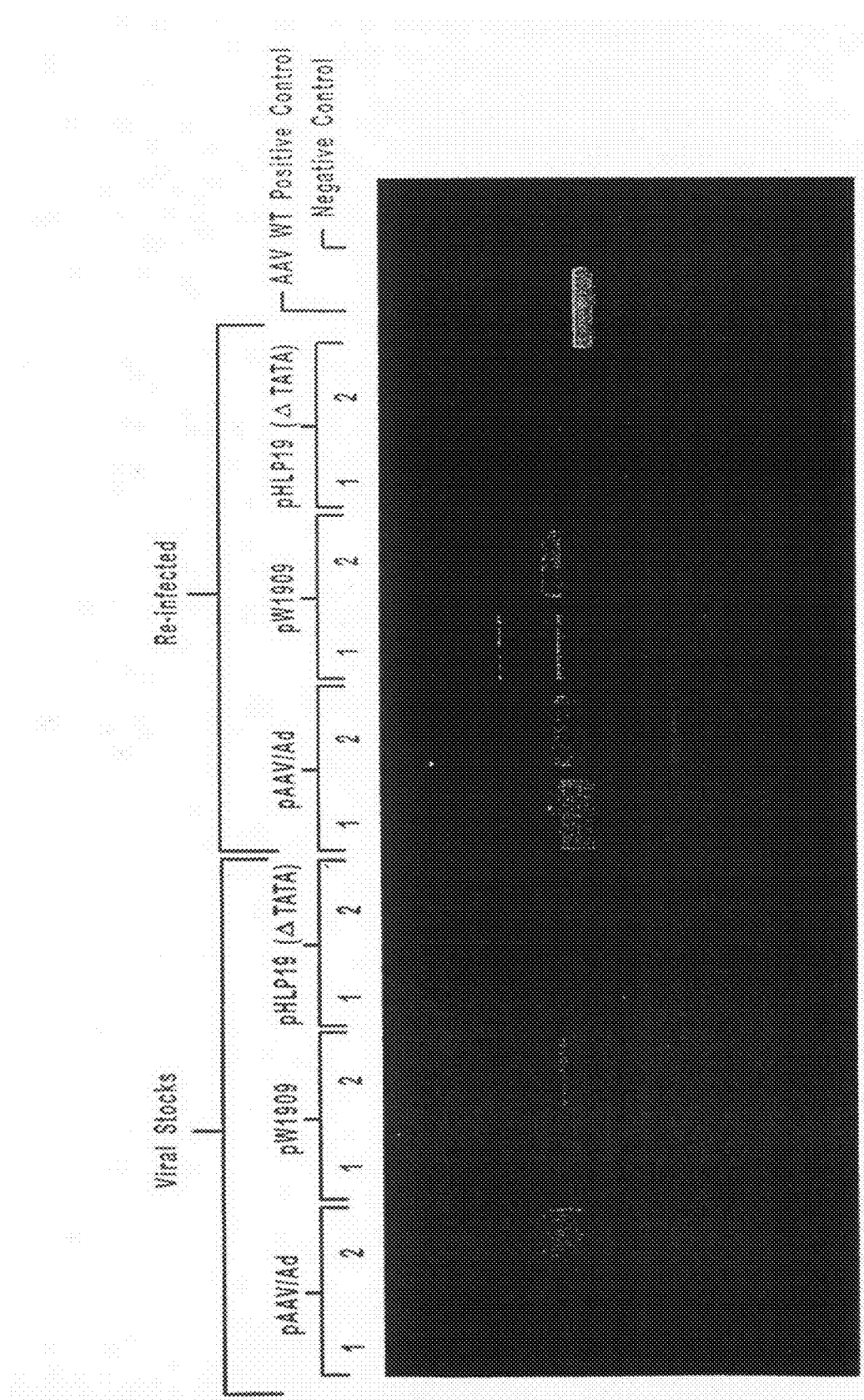

FIG. 6 presents the results of duplicate assays for pseudo-wild-type formation. PCR products generated by the assay have been separated by agarose gel electrophoresis.

6. DETAILED DESCRIPTION OF THE INVENTION

The present invention is directed to novel AAV helper function vectors for producing rAAV for introducing genetic material into animals or animal cells for a variety of research and therapeutic uses. A physician or researcher may wish to introduce DNA into an organism (or cells isolated from an organism) for any of several reasons. First, DNA may be introduced to correct a defective gene. Second, DNA may be introduced to specifically delete or mutate a given gene by, for example, homologous recombination. Third, DNA may be introduced to express a protein. Such a protein may be expressed to achieve a therapeutic benefit within the organism treated with rAAV. Alternatively, a protein may be expressed in an organism or in cells isolated from an organism with the goal of isolating and purifying the protein product. Unlike previously described methods for producing rAAV, however, the AAV helper function vectors of the present invention generate high titer stocks of rAAV but do not produce any detectable wild-type AAV.

All publications, patents, and patent applications cited herein are hereby incorporated by reference.

DEFINITIONS

In describing the present invention, the following terms will be employed, and are intended to be defined as indicated below.

"Gene transfer" or "gene delivery" refers to methods or systems for inserting foreign DNA into host cells. Gene transfer can result in transient expression of non-integrated transferred DNA, extrachromosomal replication and expression of transferred replicons (e.g., episomes), or integration of transferred genetic material into the genomic DNA of host cells.

By "vector" is meant any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors.

By "adeno-associated virus inverted terminal repeats" or "AAV ITRs" is meant the art-recognized regions found at each end of the AAV genome which function together in cis as origins of DNA replication and as packaging signals for the viral-genome. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, R. M. (1994) *Human Gene Therapy* 5, 793-801; Berns, K. I. "Parvoviridae and their Replication" in *Fundamental Virology*, 2d ed., (B N. Fields and D. M. Knipe, eds.) for the AAV-2 sequence. As used herein, an "AAV ITR" need not have the wild-type nucleotide sequence depicted in the previously cited references, but may be altered, e.g., by the insertion, deletion or substitution of nucleotides. Additionally, the AAV ITR may be derived from any of several AAV serotypes, including without limitation, AAV-1, AAV-2, AAV-3, AAV4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

By "AAV rep coding region" is meant the art-recognized region of the AAV genome which encodes the replication proteins of the virus which are required to replicate the viral genome and to insert the viral genome into a host genome during latent infection. The term also includes functional homologues thereof such as the human herpesvirus 6 (HHV-6) rep gene which is also known to mediate AAV-2 DNA replication (Thomson et al. (1994) Virology 204, 304-311). For a further description of the AAV rep coding region, see, e.g., Muzyczka, N. (1992) *Current Topics in Microbiol. and Immunol.* 158, 97-129; Kotin, R. M. (1994) *Human Gene Therapy* 5, 793-801. The rep coding region, as used herein, can be derived from any viral serotype, such as the AAV serotypes described above. The region need not include all of the wild-type genes but may be altered, e.g., by the insertion, deletion or substitution of nucleotides, so long as the rep genes present provide for sufficient integration functions when expressed in a suitable recipient cell.

The term "long forms of Rep" refers to the Rep 78 and Rep 68 gene products of the AAV rep coding region, including functional homologues thereof. The long forms of Rep are normally expressed under the direction of the AAV p5 promoter.

The term "short forms of Rep" refers to the Rep 52 and Rep 40 gene products of the AAV rep coding region, including functional homologues thereof. The short forms of Rep are expressed under the direction of the AAV p19 promoter.

By "AAV cap coding region" is meant the art-recognized region of the AAV genome which encodes the coat proteins of the virus which are required for packaging the viral genome. For a further description of the cap coding region, see, e.g., Muzyczka, N. (1992) *Current Topics in Microbiol. and Immunol.* 158, 97-129; Kotin, R. M. (1994) *Human Gene Therapy* 5, 793-801. The AAV cap coding region, as used herein, can be derived from any AAV serotype, as described above. The region need not include all of the wild-type cap genes but may be altered, e.g., by the insertion, deletion or substitution of nucleotides, so long as the genes provide for sufficient packaging functions when present in a host cell along with an AAV vector.

The term "AAV coding region" refers to a nucleic acid molecule that includes the two major AAV open reading frames corresponding to the AAV rep and cap coding regions; e.g., a nucleic acid molecule comprising a nucleotide sequence substantially homologous to base pairs 310 through 4,440 of the wild-type AAV genome. Thus, for purposes of the present invention, an AAV coding region does not include those sequences corresponding to the AAV p5 promoter region, and does not include the AAV ITRs.

By an "AAV vector" is meant a vector derived from an adeno-associated virus serotype, including without limitation, AAV-1, AAV-2, AAV-3, AAV-4, AAV-5, AAVX7, etc.

AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

"AAV helper functions" refer to AAV-derived coding sequences that can be expressed to provide AAV gene products that, in turn, function in trans for productive AAV replication. Thus, AAV helper functions include the rep and cap regions. The rep expression products have been shown to possess many functions, including, among others: recognition, binding and nicking of the AAV origin of DNA replication; DNA helicase activity; and modulation of transcription from AAV (or other heterologous) promoters. The cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virology* 63, 3822-3828; McCarty et al. (1991) *J. Virology* 65, 2936-2945. A number of other vectors have been described which encode Rep and/or Cap expression products. See, e.g., U.S. Pat. No. 5,139,941.

The term "accessory functions" refers to non-AAV derived viral and/or cellular functions upon which AAV is dependent for its replication. Thus, the term captures DNAs, RNAs and protein that are required for AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

For example, adenovirus-derived accessory functions have been widely studied, and a number of adenovirus genes involved in accessory functions have been identified and partially characterized. See, e.g., Carter, B. J. (1990) "Adeno-Associated Virus Helper Functions," in *CRC Handbook of Parvoviruses*, vol. I (P. Tijssen, ed.); Muzyczka, N. (1992) *Current Topics. Microbiol. and Immun.* 158, 97-129. Specifically, early adenoviral E1A, E1B 55K, E2A, E4, and VA RNA gene regions are thought to participate in the accessory process. Janik et al. (1981) *Proc. Natl. Acad. Sci. USA* 78, 1925-1929. Herpesvirus-derived accessory functions have been described. See, e.g., Young et al. (1979) *Prog. Med. Virol.* 25, 113. Vaccinia virus-derived accessory functions have also been described. See, e.g., Carter, B. J. (1990), supra., Schlehofer et al. (1986) *Virology* 152, 110-117.

The term "accessory function vector" refers generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon, cosmid or virus that has been modified from its naturally occurring form.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, i.e., "sense" or "antisense" strands, can be packaged into any one AAV virion and both strands are equally infectious.

A "recombinant AAV virion," or "rAAV virion" is defined herein as an infectious, replication-defective virus composed of an AAV protein shell encapsulating a heterologous nucleotide sequence of interest that is flanked on both sides by AAV ITRs. A rAAV virion is produced in a suitable host cell comprising an AAV vector, AAV helper functions, and accessory functions. In this manner, the host cell is rendered capable of encoding AAV polypeptides that are required for packaging the AAV vector (containing a recombinant nucleotide sequence of interest) into infectious recombinant virion particles for subsequent gene delivery.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52, 456; Sambrook et al. (1989) *Molecular Cloning: A Laboratory Manual*, Cold Spring Harbor Laboratories, New York; Davis et al. (1986) *Basic Methods in Molecular Biology*, Elsevier, Chu et al. (1981) Gene 13, 197. Such techniques can be used to introduce one or more exogenous DNA moieties, such as a nucleotide integration vector and other nucleic acid molecules, into suitable host cells. The term captures chemical, electrical, and viral-mediated transfection procedures.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement to the original parent, due to natural, accidental, or deliberate mutation.

As used herein, the term "cell line" refers to a population of cells capable of continuous or prolonged growth and division in vitro. Often, cell lines are clonal populations derived from, a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogues of DNA and RNA such as, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter region" is used herein in its ordinary sense to refer to a DNA regulatory sequence to which RNA polymerase binds, initiating transcription of a downstream (3' direction) coding sequence.

An "AAV p5 promoter region" encompasses both promoter sequences with identity to a p5 promoter region isolated from an AAV serotype, including without limitation, AAV-1, AAV-2, AAV-3, AAV4, AAV-5, AAVX7, etc., as well as those that are substantially homologous and functionally equivalent thereto. The AAV p5 promoter directs the expression of the long forms of Rep, and has been described and characterized.

The phrase "lacks an intact p5 promoter region" refers to a nucleotide sequence that either lacks a p5 promoter region or that contains a non-functional p5 promoter region. For example, the phrase encompasses a nucleotide sequence containing a p5 promoter region that has been rendered non-functional by one or more mutations, such that the p5 promoter region no longer functions in transcriptional initiation. As is known in the art, such mutations may include deletion of all or part of the p5 promoter region or one or more point mutations of the p5 promoter region.

The term "TATA box" is used in its ordinary sense to refer to a nucleotide sequence that is generally located 19 to 27 base pairs upstream (5' direction) of a transcriptional start site. A TATA box is typically seven base pairs long. The AAV p5 promoter has a TATA box with the nucleotide sequence TATTTAA (SEQ ID NO:1). The phrases "lacks an intact TATA box" and "ΔTATA" refer to a nucleotide sequence in which one or more mutations have been introduced to disrupt a TATA box, such that the sequence no longer functions in transcriptional initiation. As is known in the art, such mutations may include deletion of all or part of the TATA box or one or more point mutations of TATA box residues.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated," when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to, as is conventional in the art.

"Homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which allow for the formation of stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above.

A "functional homologue" or a "functional equivalent" of a given polypeptide includes molecules derived from the native, polypeptide sequence, as well as recombinantly produced or chemically synthesized polypeptides which function in a manner similar to the reference molecule to achieve a desired result. Thus, a functional homologue of AAV Rep68 or Rep78 encompasses derivatives and analogues of those polypeptides, including any single or multiple amino acid additions, substitutions and/or deletions occurring internally or at the amino or carboxy termini thereof—so long as integration activity remains.

A "functional homologue" or a "functional equivalent" of a given adenoviral nucleotide region includes similar regions derived from a heterologous adenovirus serotype, nucleotide regions derived from another virus or from a cellular source, and recombinantly produced or chemically synthesized polynucleotides which function in a manner similar to the reference nucleotide region to achieve a desired result. Thus, a functional homologue of an adenoviral VA RNA gene region or an adenoviral E2A gene region encompasses derivatives and analogues of such gene regions—including any single or multiple nucleotide base additions, substitutions and/or deletions occurring within the regions, so long as the homologue retains the ability to provide its inherent accessory function to support AAV virion production at levels detectable above background.

The term "wild-type AAV" as used herein refers to both wild-type and pseudo-wild-type AAV. "Pseudo-wild-type AAV" are replication-competent AAV virions produced by either homologous or non-homologous recombination between an AAV vector carrying ITRs and an AAV helper vector carrying rep and cap genes. Pseudo-wild-type AAV have nucleic acid sequences that differ from wild-type AAV sequences.

General Methods

It is a primary object of the present invention to provide improved AAV helper function vectors and host cells useful in the high-efficiency production of rAAV virions that can subsequently be used in gene transfer methods. More particularly, it is an object of the present invention to provide AAV helper function vectors and host cells that support production of commercially useful amounts of pseudo-wild-type-free rAAV virions.

Figure 1:
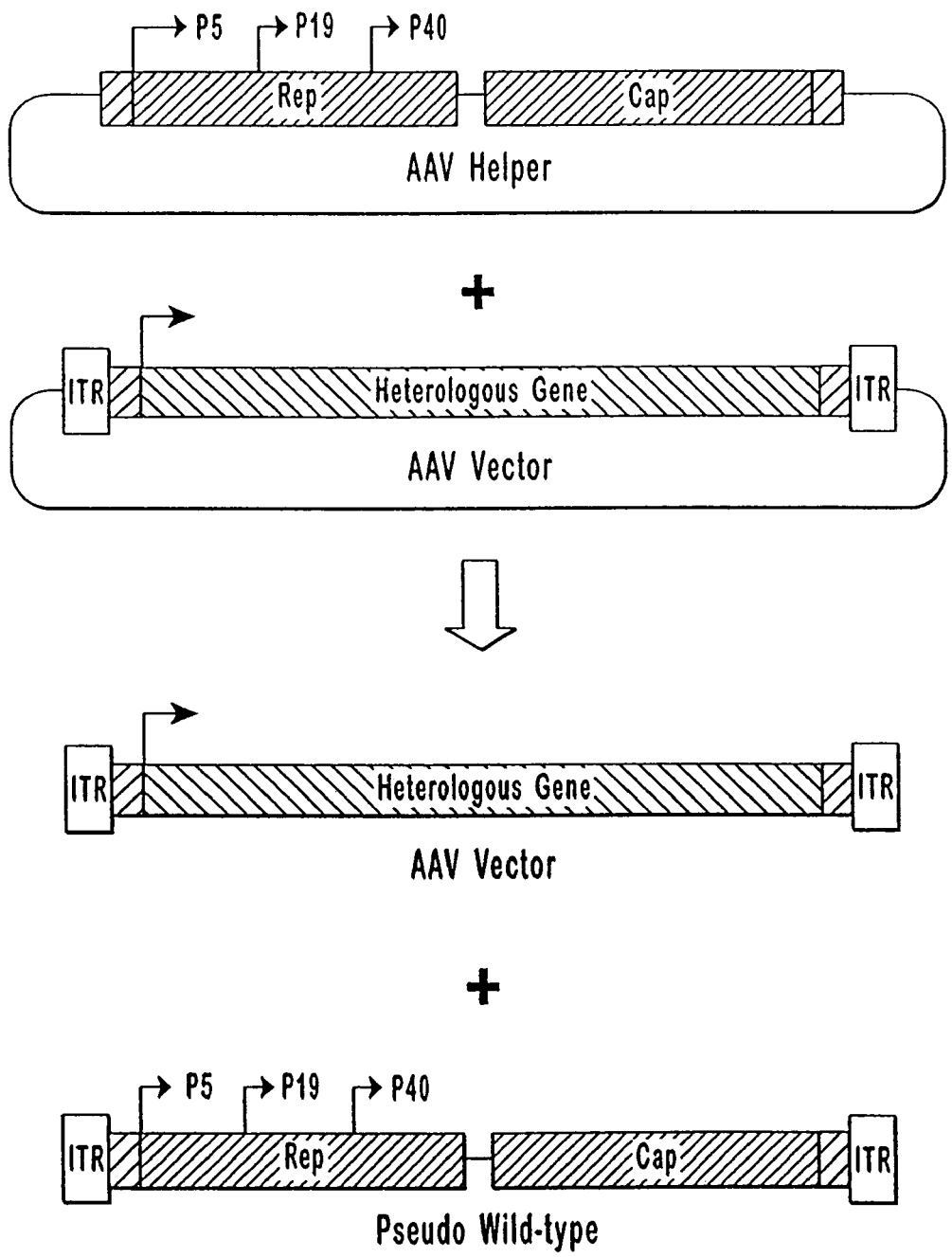
FIG. 1 depicts the viral products generated by host cells co-transfected with an AAV helper vector and an AAV vector having overlapping nucleic acid sequences (cross-hatched). Pseudo-wild-type AAV are produced by homologous recombination.
Figure 2:
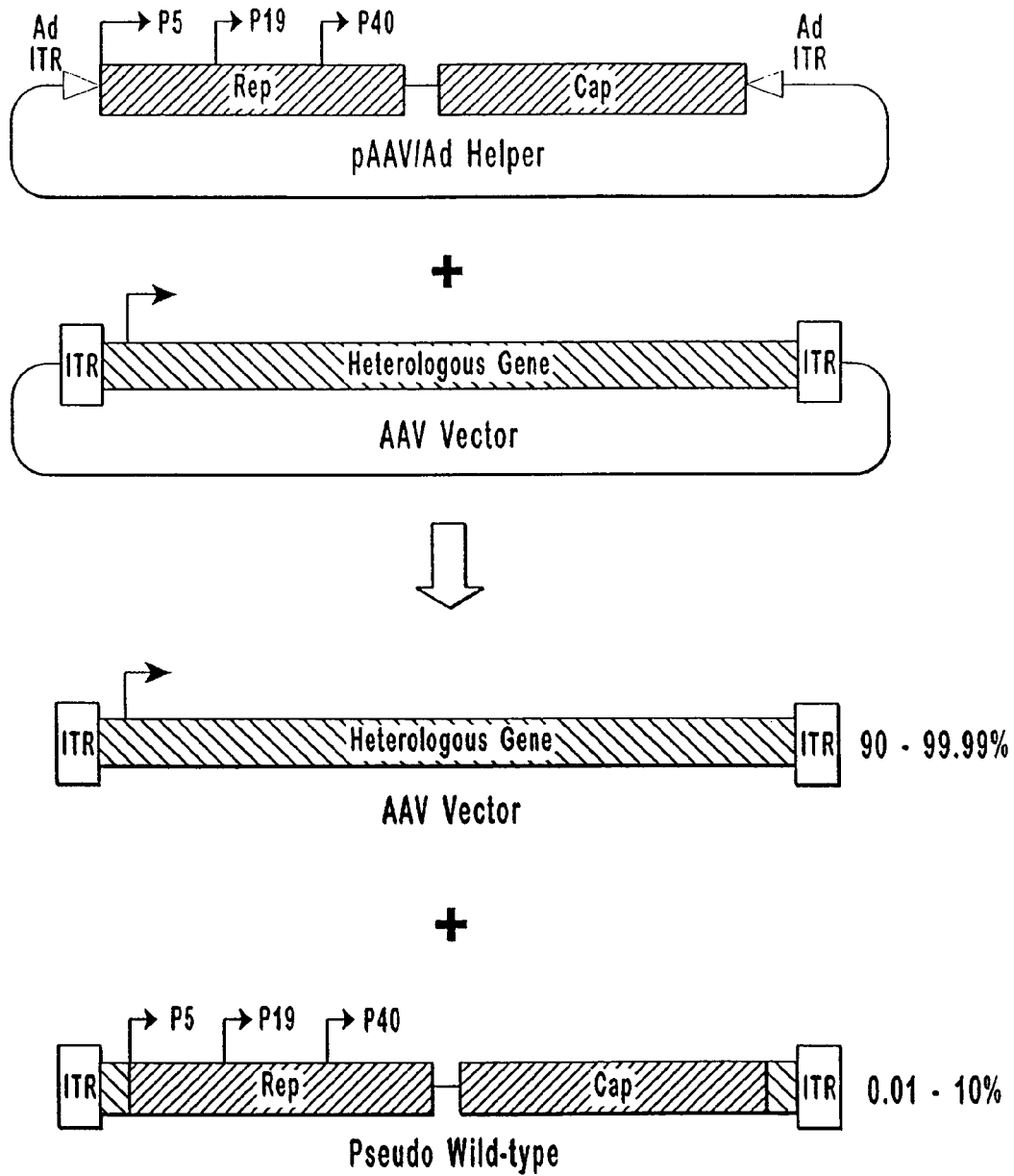
FIG. 2 depicts the viral products generated by host cells co-transfected with a pAAV/Ad helper vector and an AAV vector. Between 0.01 and 10% pseudo-wild-type AAV are produced in rAAV preparations via non-homologous recombination.
Figure 3:
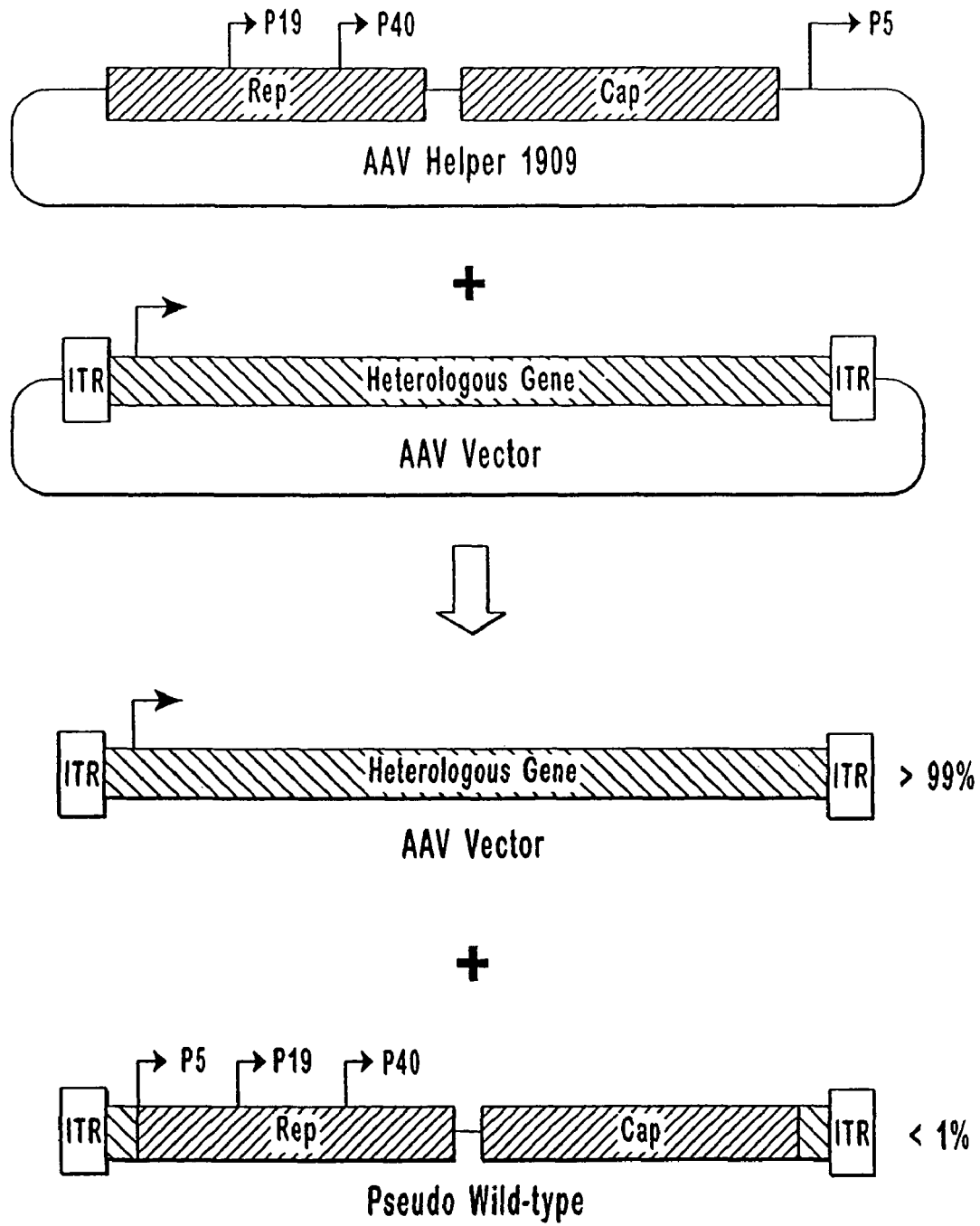
FIG. 3 depicts the viral products generated by host cells co-transfected with a p1909 helper vector and an AAV vector. Low but detectable levels of pseudo-wild-type AAV are produced via non-homologous recombination.

As depicted in FIG. 1, co-transfection of an AAV helper construct with an AAV vector can lead to the formation of small amounts of replication-competent pseudo-wild-type AAV. Prior attempts to eliminate the generation of such pseudo-wild-type products have not been completely successful. FIG. 2 illustrates the viral products generated when host cells are co-transfected with pAAV/Ad and an AAV vector. Low but detectable amounts (between 0.01 and 10 percent of total virions) of pseudo-wild-type AAV are produced. Likewise, FIG. 3 illustrates the viral products generated when host cells are co-transfected with pW1909 and an AAV vector. Again, low but detectable amounts (less than one percent of total virions) of pseudo-wild-type AAV are produced. It is an object of the present invention to eliminate the production of such replication-competent virions.

In one embodiment, a nucleic acid molecule encoding one or more AAV helper functions for supporting rAAV virion production in an animal host cell is provided. The nucleic acid molecule includes an AAV rep coding region, an AAV cap coding region, and a modified AAV p5 promoter that lacks an intact TATA box. In certain preferred embodiments, the sequence of the AAV p5 promoter's TATA box, TATTTAA (SEQ ID NO:1), is replaced with the sequence GGGGGGG (SEQ ID NO:2). The pHLP19 vector depicted in FIG. 4 comprises such a nucleotide sequence.

The above-described nucleic acid molecules can be prepared and cloned into a suitable vector such as a plasmid or viral genome to provide an AAV helper function vector. An AAV helper function vector of the present invention can further include elements that control the replication and expression of the nucleic acid sequences that code for one or more AAV helper functions.

The AAV helper function vectors of the invention can alternatively include one or more polynucleotide homologues which replace the AAV nucleotide sequences, so long as each homologue retains the ability to provide the helper functions of the replaced AAV gene or genes. Thus, homologous nucleotide sequences can be derived from another AAV serotype or can be derived from any other suitable source.

Further, AAV helper function vectors constructed according to the invention can be in the form of a plasmid, phage, transposon, cosmid, or recombinant virus. Alternatively, the vector can be in the form of one or more linearized DNA or RNA fragments which, when associated with the appropriate control elements and enzymes, can be transcribed or expressed in a host cell to provide helper functions. All of the above-described vectors can be readily introduced into a suitable host cell using transfection techniques that are known in the art. Such transfection methods have been described, including calcium phosphate co-precipitation (Graham et al. (1973) *Virol.* 52:456-467), direct micro-injection into cultured cells (M. R. Capecchi (1980) *Cell* 22:479-488), electroporation (Shigekawa et al. (1988) *BioTechniques* 6:742-751), liposome-mediated gene transfer (Mannino et al. (1988) *BioTechniques* 6:682-690), lipid-mediated transfection (Felgner et al. (1987) *Proc. Natl. Acad. Sci. USA* 84:7413-7417), and nucleic acid delivery using high-velocity microprojectiles (Klein et al. (1987) *Nature* 327:70-73).

AAV helper function vectors can be engineered using conventional recombinant techniques. Particularly, nucleic acid molecules can be readily assembled in any desired order by inserting one or more accessory function nucleotide sequences into a construct, such as by ligating restriction fragments or PCR-generated products into a cloning vector using polylinker oligonucleotides or the like. The newly formed nucleic acid molecule can then be excised from the vector and placed in an appropriate expression construct using restriction enzymes or other techniques that are well known in the art.

More particularly, selected AAV nucleotide sequences or functional homologues thereof can be excised either from a viral genome or from a vector containing the same. Alternatively, selected AAV nucleotide sequences may be generated as PCR products using as a template either viral DNA or a vector containing such DNA. The nucleotide sequences are then inserted into a suitable vector either individually or linked together to provide a helper function construct using standard ligation techniques such as those described in Sambrook et al., supra.

Nucleic acid molecules comprising one or more helper functions can also be synthetically derived using a combination of solid phase direct oligonucleotide synthesis chemistry and enzymatic ligation methods that are conventional in the art. Synthetic sequences may be constructed having features such as restriction enzyme sites, and can be prepared in commercially available oligonucleotide synthesis devices such as those devices available from Applied Biosystems, Inc. (Foster City, Calif.) using the phosphoramidite method. See, e.g., Beaucage et al. (1981) *Tetrahedron Lett.* 22:1859-1862. Preferred codons for expression of the synthetic molecule in mammalian cells can also be readily synthesized. Complete nucleic acid molecules are then assembled from overlapping oligonucleotides prepared by the above methods. See, e.g., Edge, *Nature* 292, 756 (1981); Nambair et al., *Science* 223, 1299 (1984); Jay et al., *J. Biol. Chem.* 259, 6311 (1984).

When AAV nucleotide sequences are used in the vectors of the present invention to provide helper functions for rAAV production, those nucleotide sequences may be operably linked to control sequences that direct the transcription or expression thereof. Such control sequences can comprise those AAV control sequences normally associated with the nucleotide sequences in the wild-type AAV genome. Alternatively, heterologous control sequences can be employed where desired. Useful heterologous promoter sequences include those derived from sequences encoding mammalian genes or viral genes. Examples include, but are not limited to, adenoviral promoters, the SV40 early promoter, mouse mammary tumor virus LTR (MMTV LTR) promoter, adenovirus major late promoter (Ad MLP), a herpes simplex virus (HSV) promoter, a cytomegalovirus (CMV) promoter (e.g., the CMV immediate early promoter/enhancer region), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available, e.g., from Stratagene (San Diego, Calif.).

Furthermore, the vectors of the present invention can be constructed to include selectable markers. Suitable markers include genes which confer antibiotic resistance or sensitivity, or impart color, or change the antigenic characteristics when cells which have been transfected with the nucleic acid constructs are grown in an appropriate selective medium. Particular selectable marker genes useful in the practice of the invention include the Neomycin resistance gene (encoding Aminoglycoside phosphotranferase (APH)) that allows selection in mammalian cells by conferring resistance to G418 (available from Sigma, St. Louis, Mo.) and the Hygromycin-B resistance gene (encoding Hygromycin-B-phosphotransferase (HPH)) that confers resistance to Hygrogmycin-B. Other suitable markers are known to those of skill in the art.

The AAV helper function vectors of the present invention can be used in a variety of systems for rAAV virion production. For example, suitable host cells that have been transfected with an AAV helper function vector of the present invention are rendered capable of producing rAAV virions when co-transfected with an AAV vector and one or more accessory function vectors capable of being expressed in the cell to provide accessory functions. The AAV vector, AAV helper construct and the accessory function vector(s) can be introduced into the host cell, either simultaneously or serially, using transfection techniques described above.

AAV vectors used to produce rAAV virions for delivery of a nucleotide sequence of interest can be constructed to include one or more heterologous nucleotide sequences flanked on both ends (5' and 3') with functional AAV ITRs. In the practice of the invention, an AAV vector generally includes at least one AAV ITR and an appropriate promoter sequence suitably positioned relative to a heterologous nucleotide sequence, and at least one AAV ITR positioned downstream of the heterologous sequence. The 5' and 3' ITRs need not necessarily be identical to, or derived from, the same AAV isolate, so long as they function as intended.

Suitable heterologous nucleotide sequences for use in AAV vectors include any functionally relevant nucleotide sequence. Thus, AAV vectors for use in the practice of the invention can include any desired gene that encodes a protein that is defective or missing from a recipient cell genome or that encodes a non-native protein having a desired biological or therapeutic effect (e.g., an antiviral function), or the sequence can correspond to a molecule having an antisense or ribozyme function.

AAV vectors can also include control sequences, such as promoter and polyadenylation sites, as well as selectable markers or reporter genes, enhancer sequences, and other control elements which allow for the induction of transcription. Such AAV vectors can be constructed using techniques well known in the art.

In the methods of the invention, accessory functions are used for rAAV production. Accessory functions may be provided by infecting the host cell with a suitable helper virus, such as adenovirus, herpesvirus, or vaccinia virus, or by transfecting the host cell with one or more accessory function vectors.

7. EXAMPLES

The following example is given to illustrate one embodiment which has been made within the scope of the present invention. It is to be understood that the following example is neither comprehensive nor exhaustive of the many types of embodiments which can be prepared in accordance with the present invention.

Example 1

Wild-Type AAV Production

Plasmid construction pW1909 has previously been described. See U.S. patent application Ser. No. 08/688,648, which is incorporated herein by reference. Briefly, as shown in FIG. 3, pW1909 comprises rep and cap coding regions and a downstream p5 promoter sandwiched between two Flip Recombination Target (FRT) sites.

Plasmid pHLP19 encodes a modified AAV-2 genome designed to enhance AAV vector production while suppressing the generation of replication-competent pseudo-wild-type virus. pHLP19 has the same general structure as pGN1909 described in U.S. Pat. No. 5,622,856, incorporated herein by reference. In both plasmids, the p5 promoter is moved to a position 3' of the cap gene and is replaced by a 5' untranslated region primarily composed of a FLP recombinase recognition sequence. Unlike pGN1909, which contains substantial regions of homology between the 3' and 5' ends of the AAV genome, pHLP19 was constructed so as to eliminate any such regions of homology. Additionally, the seven base pair TATA box of the pHLP19 p5 promoter was destroyed by mutation of that sequence to GGGGGGG (SEQ ID NO:2).

pHLP19 was constructed in a several step process using AAV-2 sequences derived from the AAV-2 provirus, pSM620. First, the ITRs were removed from the rep and cap sequences. pSM620 was digested with SmaI and PvuII, and the 4543 bp rep- and cap-encoding SmaI fragment was cloned into the SmaI site of pUC119 to produce the 7705 bp plasmid, pUCrepcap. The remaining ITR sequence flanking the rep and cap genes was then deleted by oligonucleotide-directed mutagenesis using the oligonucleotides 145A (5'-GCTCGG-TACCCGGGC GGAGGGGTGGCAGTCG-3' (SEQ ID NO:3)) and 145B (5'-TAATCATTAACTA CAGCCCGGG-GATCCTCT-3' (SEQ ID NO:4)). The resulting plasmid, pUCRepCapMutated (pUCRCM) (7559 bp) contains the entire AAV-2 genome without any ITR sequence (4389 bp). SrfI sites, in part introduced by the mutagenic oligonucleotides, flank the rep and cap genes in this construct. The AAV sequences corresponds to AAV-2 positions 146-4,534.

Second, an Eco47III restriction enzyme site was introduced at the 3' border of p5. This Eco47III site was introduced at the 3' end of the p5 promoter in order to facilitate excision of the p5 promoter sequences. To do this, pUCRCM was mutagenized with primer P547 (5'-GGTTTGAAC GAGCGCTCGCCATGC-3'(SEQ ID NO:5)). The resulting 7559 bp plasmid was called pUCRCM47III.

Third, an assembly plasmid, pBluntscript, was constructed. The polylinker of pBSII SK+ was changed by excision of the original with BssHII and replacement with oligonucleotides blunt 1 and 2. The resulting plasmid, bluntscript, is 2830 bp in length, and the new polylinker encodes the restriction sites EcoRV, HpaI, SrfI, PmeI, and Eco47III. The blunt 1 sequence is 5'-CGCGCCGATATCGTTAACGC-CCGGGCGTTTAAACAGCGCTGG-3' (SEQ ID NO:6) and the blunt 2 sequence is 5'-CGCGCCAGCGCTGTT-TAAACGCCCGGGCGTTAACGATATCGG-3' (SEQ ID NO:7).

Fourth, the plasmid pH1 was constructed by ligating the 4397 bp rep- and cap-encoding SmaI fragment from pUCRCM into the SrfI site of pBluntscript, such that the HpaI site was proximal to the rep gene. pH1 is 7228 bp in length.

Fifth, the plasmid pH2 was constructed. pH2 is identical to pH1 except that the p5 promoter of pH1 is replaced by the 5' untranslated region of pGN1909. To accomplish this, the 329 bp AscI(blunt)-SfiI fragment encoding the 5' untranslated region from pW1909lacZ was ligated into the 6831 bp SmaI (partial)-SfiI fragment of pH1, creating pH2. pH2 is 7155 bp in length.

Sixth, pH8 was constructed. A p5 promoter was added to the 3' end of pH2 by insertion of the 172 bp, SmaI-Eco47III fragment encoding the p5 promoter from pUCRCM47III into the Eco47III site in pH2. This fragment was oriented such that the direction of transcription of all three AAV promoters are the same. This construct is 7327 bp in length.

Seventh, the plasmid pHLP19 was constructed. The TATA box of the 3' p5 (AAV-2 positions 255-261, sequence TATT-TAA (SEQ ID NO:1)) was eliminated by changing the sequence to GGGGGGG (SEQ ID NO:2) using the mutagenic oligonucleotide 5DIVE2 (5'-TGTGGT-CACGCTGGGGGG GGGGGCCCGAGTGAGCACG-3' (SEQ ID NO:8)). The resulting construct, pHLP19, is 7327 bp in length.

The plasmid pladeno 5 provides a complete set of adenovirus helper functions for AAV vector production when transfected into 293 cells. Essentially, it is composed of the E2A, E4, and VA RNA regions from adenovirus-2 and a plasmid back bone. To construct pladeno 5, pBSII SK+ was modified to replace the 632 bp region encoding the polylinker and alpha complementation cassette with a single EcoRV site using oligonucleotide-directed mutagenesis and the following oligonucleotide: 5'-CCGCTACAGGGCGCGATATCA GCTCACTCAA-3' (SEQ ID NO:9). A polylinker encoding the restriction sites BamHI, KpnI, SrfI, XbaI, ClaI, Bst1107I, SalI, PmeI, and NdeI was then cloned into the EcoRV site (5'-GGATCCGGT ACCGCCCGGGCTCTAGAATCGATG-TATACGTCGACGTTTAAACCATATG-3' (SEQ ID NO:10)).

The E2A, VA RNA, and E4 regions were then inserted. Adenovirus-2 DNA was digested and restriction fragments encoding the E2A region (a 5,335 bp, KpnI-SrfI fragment corresponding to positions 22,233-27,568 of the adenovirus-2 genome) and the VA RNAs (a 732 bp, EcoRV-SacII fragment corresponding to positions 10,426-11,157 of the adenovirus-2 genome) were isolated. The E2A fragment was installed between the SalI and KpnI sites of the polylinker. An E4 region was first assembled in pBSII SK+ by ligating a 13,864 bp, BamHI-AvrII fragment corresponding to adenovirus-2 positions 21,606-35,470 (encoding the 5' end of the gene) and a 462 bp, AvrII and SrfI, digested PCR fragment corresponding to adenovirus-2 positions 35,371-35,833 (encoding the 3' end of the gene) between the BamHI and SmaI sites of pBSII SK+. The oligonucleotides used to produce the PCR fragment were designed to introduce a SrfI site at the junction were the E4 promoter and the adenovirus terminal repeat intersect and have the sequences 5'-AGAGGCCCG GGCGTTTTAGGGCGGAGTAACTTGC-3' (SEQ ID NO:11) and 5'-ACATACCCGCAGGCG TAGAGAC-3' (SEQ ID NO:12). The intact E4 region was excised by cleavage with SrfI and SpeI and the 3,189 bp fragment corresponding to adenovirus-2 positions 32,644-35,833 was cloned into the E2A intermediate between the SrfI and XbaI sites. Finally, the VA RNA fragment was inserted into the Bst1107 site after T4 polymerase-mediated blunt end modification of the SacII site. The genes in pladeno 5 are arranged such that the 5' ends of the E2A and E4 promoters abut, causing the regions to transcribe away from each other in opposite directions. The VA RNA genes, which are located at the 3' end of the E4 gene, transcribe towards the E4 gene. The plasmid is 11,634 bp in length.

Transfection. 293 cells (available from ATCC, catalog number CRL-1573) were seeded in 10 cm dishes at a density of $3 \times 10^6$ cells per dish in 10 ml medium and incubated at 37° C. with $CO_2$ and humidity. After an overnight incubation, cells were approximately seventy to eighty percent confluent.

The cells were then transfected with DNA by the calcium phosphate method, which is well known in the art. Briefly, 10 µg of each plasmid (pVmLacZ, pladenoS, and an AAV helper) were added to a 3 ml sterile, polystyrene snap cap tube using sterile pipette tips. 1.0 ml of 300 mM $CaCl_2$ (JRH grade) was added to each tube and mixed by pipetting up and down. An equal volume of 2×HBS (274 mM NaCl, 10 mM KCl, 42 mM HEPES, 1.4 mM $Na_2PO_4$, 12 mM dextrose, pH 7.05, JRH grade) was added with a 2 ml pipette, and the solution was pipetted up and down three times. The DNA mixture was immediately added to the cells, one drop at a time, evenly throughout the dish. The cells were then incubated at 37° C. with $CO_2$ and humidity for six hours. A granular precipitate was visible in the transfected cell cultures. After six hours, the DNA mixture was removed from the cells, which were provided with fresh medium and incubated for 72 hours.

After 72 hours, the cells were harvested, pelleted, and resuspended in 1 ml TBS/1% BSA. Freeze/thaw extracts were prepared by repeatedly (three times) freezing the cell suspension on dry ice and thawing at 37° C. Viral preps were stored at −80° C. and titered by dot blot assay prior to the first round of infection.

AAVlacZ Viral Infections. 293 cells were seeded in 6-well plates at a density of $5 \times 10^5$ cells per well in 2 ml medium and incubated overnight at 37° C. with $CO_2$ and humidity. The cells were then infected with AAVlacZ viral preps at a multiplicity of infection (MOI) of $10^4$ (i.e., $5 \times 10^9$ prt's per well) and with or without adenovirus at a MOI of 10 ($5 \times 10^6$ prt's per well). The infected cells were incubated for three days and then harvested.

Wild Type AAV PCR Detection Assay. Detection of replicating wild-type AAV species was performed by screening purified viral DNA preps using PCR methods as depicted in FIG. 5. PCR primers specific to wild-type AAV sequences were designed to amplify a 496 bp product representing the 3' end of the viral genome. The sense primer, SG1 (5'-CACACG-GACGGACATITCACC-3' (SEQ ID NO:13)), annealed to the 3' end of the "cap" gene, whereas the antisense primer, SG5 (5'-GAGTGGCCAACTCCATCACTA-3' (SEQ ID NO:14)), primed within the ITR sequence crossing the A-stem/D region boundary. This primer set was able to distinguish native wild-type AAV sequences from novel, recombinant, pseudo-wild-type AAV species based on size differences in the PCR products. Native wild-type AAV species yield a discrete "Cap/ITR" PCR product of 496 bp, whereas pseudo-wild-type species can yield an array of PCR fragment sizes. These PCR sequences represent multiple species of replicating viral DNA formed by recombination events between the 3' end of the cap gene in the AAV helper plasmid and the ITR-containing sequences from the AAV vector plasmid. PCR reactions are performed in 50 μL volumes containing 1×PCR buffer, 0.2 mM of each dNTP, 1 unit of Taq polymerase, 0.1 mM of the "cap" primer (SG1) and 10 mM of the ITR primer (SG5). The template DNA is derived either directly from the viral material or from amplified AAV virus following rounds of infection in the presence of Ad helper virus. Prior to use, the DNA is purified from the viral capsids by DNAse, proteinase K and phenol/chloroform treatments, which release purified naked viral DNA. The PCR reactions are cycled through 35 rounds of amplification, denaturing at 94° C. for 20 seconds, annealing at 65° C. for 20 seconds, and extending at 72° C. for 1 minute.

The results of such an assay (performed on duplicate samples) are shown in FIG. 6. The first six lanes contain the products (separated by agarose gel electrophoresis) of PCR reactions performed on viral stocks prior to re-infection. Bands indicating the presence of pseudo-wild-type are present in the first four lanes (pAAV/Ad and pW1909) but not in the fifth and sixth lanes (pHLP19). The next six lanes contain the products of PCR reactions performed on viral stocks after re-infection. Once again, the first four lanes of this series (pAAV/Ad and pW1909) contain bands that indicate the presence of pseudo-wild-type virions. By contrast, no such bands are visible in the fifth and sixth lanes of this series (pHLP19). The last two lanes contain positive (wild-type AAV) and negative controls. A 496 bp band, corresponding to the wild-type PCR product, is visible in the positive control lane.

The results of rAAV and pseudo-wild-type production are summarized in Table 1 below.

TABLE 1

| Helper Function Vector | Relative rAAV Vector Production | Wild-Type Production? |
| --- | --- | --- |
| pAAV/Ad | 100% | Yes |
| pW1909 | 400% | Yes |
| pHLP19 | 200%-300% | Not Detected |

Figure 4:
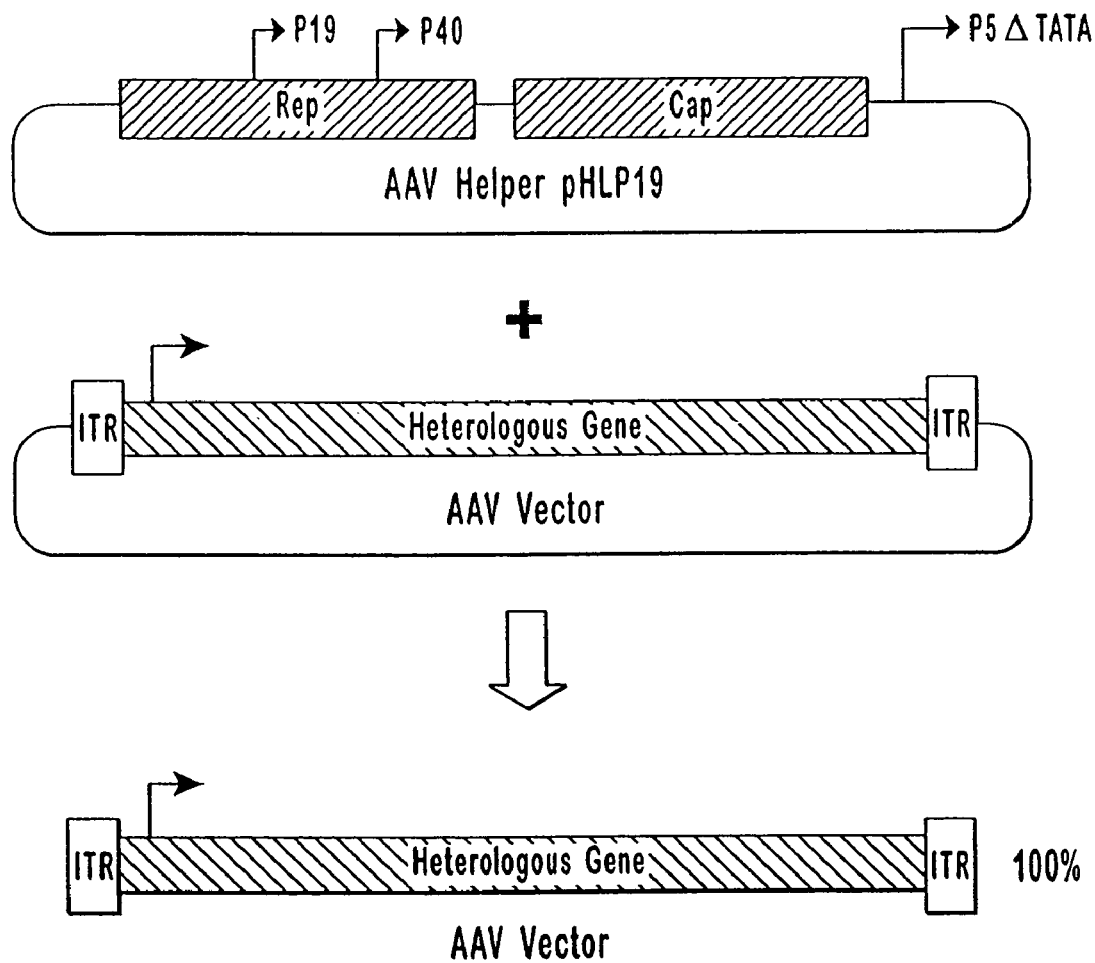
FIG. 4 depicts the viral products generated by host cells co-transfected with an pHLP19 (ΔTATA) helper vector and an AAV vector. Pseudo-wild-type AAV are not detected.

In summary, conventional AAV rep/cap vectors produce pseudo-wild-type AAV virions, as shown in FIGS. 1-3. By contrast, the AAV helper constructs of the present invention do not produce detectable pseudo-wild-type AAV, as shown in FIG. 4. Moreover, these AAV helper constructs can be used to produce high titer preparations of rAAV.

The invention may be embodied in other specific forms without departing from its essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

I claim:

1. A method of producing recombinant AAV (rAAV) virions comprising:
   introducing into a suitable host cell
   (a) an AAV vector;
   (b) an AAV helper function vector, wherein the helper function vector comprises a nucleic acid molecule which encodes one or more AAV helper functions, said nucleic acid molecule comprising:
   an AAV rep coding region;
   an AAV cap coding region; and
   a nucleotide sequence comprising a modified AAV p5 promoter region, such that the modified AAV p5 promoter region no longer functions in transcription initiation; and
   (c) accessory functions upon which AAV is dependent for replication; and
   culturing the host cell to produce rAAV virions.

2. A host cell comprising
   (a) an AAV vector;
   (b) an AAV helper function vector, wherein the helper function vector comprises a nucleic acid molecule which encodes one or more AAV helper functions, said nucleic acid molecule comprising:
   an AAV rep coding region;
   an AAV cap coding region; and
   a nucleotide sequence comprising a modified AAV p5 promoter region, such that the modified AAV p5 promoter region no longer functions in transcription initiation; and
   (c) accessory functions upon which AAV is dependent for replication.

3. The host cell of claim 2, wherein the accessory functions comprise accessory function genes.

4. A method of producing recombinant AAV (rAAV) virions comprising:
   introducing into a suitable host cell
   (a) an AAV vector;
   (b) an AAV helper function vector, wherein the helper function vector comprises a nucleic acid molecule which encodes one or more AAV helper functions, said nucleic acid molecule comprising:
   an AAV rep coding region;
   an AAV cap coding region; and
   a nucleotide sequence comprising a modified AAV p5 promoter region, wherein the modified p5 promoter region lacks an intact TATA box; and
   (c) accessory functions upon which AAV is dependent for replication; and
   culturing the host cell to produce rAAV virions.

5. A host cell comprising
   (a) an AAV vector;
   (b) an AAV helper function vector, wherein the helper function vector comprises a nucleic acid molecule which encodes one or more AAV helper functions, said nucleic acid molecule comprising:
   an AAV rep coding region;
   an AAV cap coding region; and
   a nucleotide sequence comprising a modified AAV p5 promoter region, wherein the modified p5 promoter region lacks an intact TATA box; and
   (c) accessory functions upon which AAV is dependent for replication.

6. The host cell of claim 5, wherein the accessory functions comprise accessory function genes.

7. The host cell of claim 5, such that the modified AAV p5 promoter region is situated 3' relative to the rep coding region.

8. A method of producing recombinant AAV (rAAV) virions comprising:
   introducing into a suitable host cell
   (a) an AAV vector;
   (b) an AAV helper function vector, wherein the helper function vector comprises a nucleic acid molecule which encodes one or more AAV helper functions, said nucleic acid molecule comprising:
   an AAV rep coding region;
   an AAV cap coding region; and
   a nucleotide sequence comprising a modified AAV p5 promoter region, wherein the modified p5 promoter region lacks an intact TATA box and the nucleotide sequence is arranged such that the modified AAV p5 promoter region is situated 3' relative to the rep coding region; and
   (c) accessory functions upon which AAV is dependent for replication; and
   culturing the host cell to produce rAAV virions.

9. The host cell of claim 5, such that the modified AAV p5 promoter region is situated 3' relative to the cap coding region.

* * * * *

SEQUENCE LISTING

<160> NUMBER OF SEQ ID NOS: 14

<210> SEQ ID NO 1
<211> LENGTH: 7
<212> TYPE: DNA
<213> ORGANISM: adeno-associated virus 2

<400> SEQUENCE: 1 tatttaa                                                              7

<210> SEQ ID NO 2
<211> LENGTH: 7
<212> TYPE: DNA
<213> ORGANISM: Artificial Sequence
<220> FEATURE:
<223> OTHER INFORMATION: Description of Artificial Sequence:synthetic
      sequence

<400> SEQUENCE: 2 ggggggg                                                              7

<210> SEQ ID NO 3

```
<211> LENGTH: 30
<212> TYPE: DNA
<213> ORGANISM: Artificial Sequence
<220> FEATURE:
<223> OTHER INFORMATION: Description of Artificial Sequence:synthethic
      oligonucleotide

<400> SEQUENCE: 3
gctcggtacc cgggcggagg ggtggagtcg                                    30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:synthethic
      oligonucleotide

<400> SEQUENCE: 4
taatcattaa ctacagcccg gggatcctct                                    30

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:synthethic
      oligonucleotide

<400> SEQUENCE: 5
ggtttgaacg agcgctcgcc atgc                                          24

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence:synthethic
      oligonucleotide

<400> SEQUENCE: 6
cgcgccgata tcgttaacgc ccgggcgttt aaacagcgct gg                      42

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence:synthethic
      oligonucleotide

<400> SEQUENCE: 7
cgcgccagcg ctgtttaaac gcccgggcgt taacgatatc gg                      42

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence:synthethic
      oligonucleotide

<400> SEQUENCE: 8
tgtggtcacg ctggggggggg gggcccgagt gagcacg                           37

<210> SEQ ID NO 9
<211> LENGTH: 31
```

```
<212> TYPE: DNA
<213> ORGANISM: Artificial Sequence
<220> FEATURE:
<223> OTHER INFORMATION: Description of Artificial Sequence:synthethic
      oligonucleotide

<400> SEQUENCE: 9
ccgctacagg gcgcgatatc agctcactca a                                    31

<210> SEQ ID NO 10
<211> LENGTH: 58
<212> TYPE: DNA
<213> ORGANISM: Artificial Sequence
<220> FEATURE:
<223> OTHER INFORMATION: Description of Artificial Sequence:synthethic
      oligonucleotide

<400> SEQUENCE: 10
ggatccggta ccgcccgggc tctagaatcg atgtatacgt cgacgtttaa accatatg      58

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence:synthethic
      oligonucleotide

<400> SEQUENCE: 11
agaggcccgg gcgttttagg gcggagtaac ttgc                                 34

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:synthethic
      oligonucleotide

<400> SEQUENCE: 12
acatacccgc aggcgtagag ac                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:synthethic
      oligonucleotide

<400> SEQUENCE: 13
cacacggacg gacattttca cc                                              22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:synthethic
      oligonucleotide

<400> SEQUENCE: 14
gagtggccaa ctccatcact a                                               21
```